United States Patent [19]

Engel et al.

[11] Patent Number: 5,556,856
[45] Date of Patent: Sep. 17, 1996

[54] PHTHALAZINONE DERIVATIVES THAT MODULATE MULTI-DRUG RESISTANCE

[75] Inventors: Jürgen Engel, Alzenau; Bernhard Kutscher, Maintal; Ilona Fleischhauer, Offenbach; Stefan Szelenyi, Schwalg; Peter Metzenauer, Gründau; Ulrich Werner, Miehlen, all of Germany

[73] Assignee: Asta Medica Aktiengesellschaft, Dresden, Germany

[21] Appl. No.: 416,467

[22] Filed: Apr. 4, 1995

Related U.S. Application Data

[63] Continuation of Ser. No. 154,091, Nov. 18, 1993, abandoned, which is a continuation of Ser. No. 124,496, Sep. 22, 1993, abandoned.

[30] Foreign Application Priority Data

Oct. 2, 1992 [DE] Germany .................. 42 33 113.7

[51] Int. Cl.$^6$ .................................. A61K 31/495
[52] U.S. Cl. ................ 514/248; 514/212; 514/315
[58] Field of Search ................... 514/212, 248, 514/315

[56] References Cited

PUBLICATIONS

Chemical Abstracts 112:132033d, Yamanoto et al., 1989.

*Primary Examiner*—Kevin E. Weddington
*Attorney, Agent, or Firm*—Cushman Darby & Cushman

[57] ABSTRACT

Phthalazinone derivatives and their optical isomers are used as medications to combat heart rhythm disturbances, to combat pain and to break through multi-drug resistance.

5 Claims, No Drawings

PHTHALAZINONE DERIVATIVES THAT MODULATE MULTI-DRUG RESISTANCE

This is a continuation of application Ser. No. 08/154,091, filed on Nov. 18, 1993, which was abandoned upon the filing hereof which is a continuation of Ser. No. 08/124,496, filed Sep. 22, 1993, now abandoned.

The present invention relates to the use of certain phthalazinone derivatives to provide anti-arrhythmic, analgesic and anti-multi-drug resistance effects.

BACKGROUND OF THE INVENTION

The phthalazinone derivative azelastin (INN) has been successfully used in the treatment and prophylaxis of bronchial asthma and allergic and seasonal rhinitis. It can be synthesized as described in German patent 2 164 058.

D-18024 hydrochloride (INN: flezelastin) was developed as a follow-up preparation in the form of the racemic mixture. The method of preparation is described in European patent 222 191.

It has now surprisingly been found that the phthalazinone derivatives of the general formula I

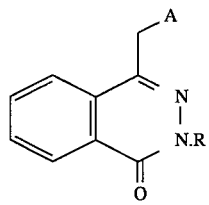

where A=phenyl (unsubstituted, mono- or multi-halogen substituted), H or $C_1$–$C_3$-alkyl, 2-furyl or 2-thienyl and

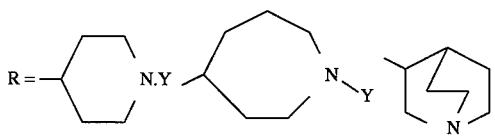

with Y=H or $C_1$–$C_6$-alkyl, where the alkyl radical can be substituted with a (substituted) phenyl ring, a hydroxy group or an alkoxycarbonyl group as well as all physiological acceptable acid addition salts thereof and in particular the compounds of Formula II, III, IV

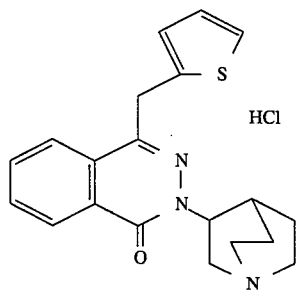

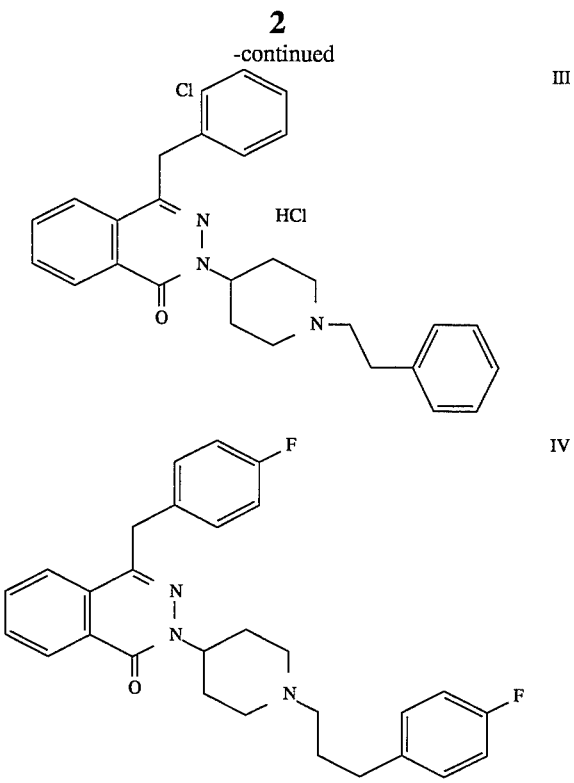

as well as the optical isomers of azelastin and the optical isomers of flezelastin—have an antiarrhythmic effect. They can presumably be classified in the group of Class III-antiarrhythmically acting compounds.

The compounds also have an analgesic activity.

The compounds of the invention also have an anti-emetic effect. The anti-emetic effect has been found by inhibition of cisplatinum-induced emesis in awake domestic pigs after oral or intravenous administration.

Inhibition of cisplatinum-induced emesis in awake domestic pigs. The data represent the number of emetic attacks during the observation period. The values given are means of 5 individual

| Compound | Dose | 0–4 Hours | 0–8 Hours | 0–24 Hours |
|---|---|---|---|---|
| Control | | 10 | 10 | 12 |
| i.v. | 5 mg/pig | 8 | 9 | 18 |
| | 15 mg/pig | 0 | 3 | 11 |
| | 50 mg/pig | 0 | 0 | 2 |
| p.o. | 10 mg/pig | 3 | 3 | 3 |
| | 25 mg/pig | 0 | 0 | 3 |
| | 60 mg/pig | 0 | 1 | 2 |
| | 100 mg/pig | 0 | 0 | 1 |
| | 200 mg/pig | 0 | 0 | 0 |

The compounds of Formula I are prepared by the method of German patent DE 2 164 058, the compound according to Formula II by analogy with the instructions contained in German patent 2 164 058, Example 10. The compound of Formula III is prepared by analogy with Example 2 of European patent 174 464. Synthesis of the compound according to Formula IV is according to the instructions given in European patent 0 222 191 (Example 36).

The optical isomers of azelastin and flezelastin were obtained using the fractional crystallization method. The absolute configuration of azelastin was determined by X-ray structure analysis.

The antiarrhythmic effect was tested by the following experimental procedure:

Twenty young rabbits of mixed breed and either sex, weighing 1475±75 g (mean±S.E.), were used. The animals were sacrificed by a blow on the head, their heart was isolated and the left atrium, a strip of the anterior free wall of the right ventricle, as well as one of the papillary muscles of the right ventricle were dissected and pinned to the bottom ('non-toxic' rubber) of a thermostated organic bath, containing modified Locke's solution. The composition of the solution was the following: $Na^+$ 140; $K^+$ 5.63; $Ca^{2+}$ 2.17; glucose 11, $HCO_3$ 25; CL 125; total 309 mmol/l, pH 7.4. Continuous stirring and oxygenation of the solution were maintained by the bubbling of a mixture of 95% $O_2$ and 5% $CO_2$. The temperature of the organ bath was kept at 32° C. The isolated left atrium, papillary muscle and the strip prepared from the anterior free wall of the right ventricle were electrically paced by rectangular electric impulses of 1 msec duration, twice-threshold intensity and a 100 per min frequency. During the experiments the following electrophysiological parameters were determined: electrical threshold, effective refractory period and conduction time. The effective refractory period (i.e. the least interval between two successive electro-mechanical responses) was measured by applying a threefold-threshold test stimulus (1 msec, square waves) delivered from a DISA Multistim at various times following the pacing impulse. Conduction time was measured on an oscilloscope (Tektronis 2230) as a distance (i.e. time) between the artifact of the pacing stimulus and the appearance of the subsequent surface potential recorded via bipolar platinum electrodes. The auxotonically measured contractility (maximum contractile force) was also followed (papillary muscle, left atrium).

After a 60 min equilibrium in the control solution, the preparations were exposed to 10 µM of the test substance for a period of 60 min. Except for the effect on the effective refractory periods (determined at the 30th and 60th min only) all the other parameters were measured in every 15th min, i.e. four times in the presence of a given concentration of the compound examined.

The values given in the Tables and Figures are means ±S.E. The effect of compounds on the various parameters was estimated statistically by the t-test (Student-Welch); P values<0.05 were regarded as significant.

The results are set out in Table 1:

TABLE 1

|  | Azelastine | D-18024 | D-20602 | D-21111 | ICS-205930 |
|---|---|---|---|---|---|
| Antiarrhythmic properties in rabbit cardiac preparations at 10 µM |  |  |  |  |  |
| incubation time with drugs 60 minutes change in percentage from control Electrical threshold |  |  |  |  |  |
| right anterior free wall | +29 | −1 | +100 | +37 | +51 |
| right ventricular papillary muscle | +22 | +29 | +102 | +35 | +34 |
| left atrial myocardium | +25 | +12 | +68 | +45 | +51 |
| Conduction time |  |  |  |  |  |
| right anteior papillary muscle | +50 | +103 | +137 | +109 | +111 |
| left atrial myocardium | +40 | +91 | +118 | +111 | +57 |
| Effective refractory period |  |  |  |  |  |
| right ventricular papillary muscle | +9 | +7 | +26 | +25 | +21 |
| left atrial myocardium | +12 | +66 | +42 | +53 | +26 |
| Contractility |  |  |  |  |  |
| left auricle |  | −39 | −35 | −24 | −33 |
| papillary muscle |  | −48 | −32 | −25 | −29 |

The peripheral analgesic effect was shown in the model of the Writhing Test (IWRAC) and in the model of the Randall-Selitto inflammation pain test (IRS).

See Table 2.

Analgesic effect of phthalazinone derivatives of formula I

| Example | | Effect in test model | |
|---|---|---|---|
| A | R | IWRAC[a] | IRS[b] |
| 4-Cl-Phenyl | –[azepane]-N–CH₂CH₂–phenyl | 91% | 77% |
| 4-F-Phenyl | –[azepane]-N–CH₂–phenyl | 75% | 53% |
| 4-F-Phenyl | –[azepane]-N–CH₂CH₂–phenyl | ED₅₀ = 2.7 | 54% |
| 4-F-Phenyl | –[piperidine]-N–CH₂CH₂CH₂–phenyl | 77% | 67% |
| 4-F-Phenyl | –[piperidine]-N–CH₂CH₂CH₂–(4-F-phenyl) | 67% | 52% |
| Phenyl | 3-Chinuclidyl | ED₅₀ = 3.0 | ED₅₀ = 1.5 |
| 4-F-Phenyl | 3-Chinuclidyl | ED₅₀ = 4.6 | ED₅₀ = 1.5 |
| 4-Cl-Phenyl | –[piperidine]-N–CH₂CH₂–C(O)–O–Et | 67% | 50% |
| 4-Cl-Phenyl | –[azepane]-N–CH₂CH₂–OH | ED₅₀ = 17 | ED₅₀ = 19 |
| 2-Cl-Phenyl | –[azepane]-N–CH₂CH₂–phenyl | ED₅₀ = 4.1 | ED₅₀ = 4.7 |
| 2-Furyl | –[azepane]-N–CH₂CH₂–phenyl | — | 40% |

[a] IWRAC = Acetic acid induced Writhing Test. Data in % refer to a dose of 6 mg/kg p.o. (mouse). The $ED_{50}$ values are given in mg/kg.
[b] IRS = Randall-Selitto inflammation pain test. Data in % refer to a dose or 10 mg/kg p.o. (rat). The $ED_{50}$ values are given in mg/kg.

During treatment with cytostatics it is observed that the tumor proves therapeutically resistant after initial treatment success. Treatment with a different cytostatic also promises no success.

This phenomenon is termed multi-drug resistance. (MDR) (Vendrik, Bergers, de Jong, Steerenberg Resistance to cytostatic drugs at the cellular level, Cancer Chemother, Pharmacol. (1992) 29, 413–429).

The compounds of the invention are also suitable for the preparation of medications against this phenomenon.

The suitability of the compounds for the preparation of medications which modulate MDR has been determined in the following experiment.

Acute Brown Norway myeloid leukaemia (BNML) resembles acute myelocytic leukaemia in main with regard to its growth characteristics and its reactions to chemotherapy (for a recent review of BNML see Martens et al., Leukemia 4, 241–257, 1990). To develop a clinically relevant medication-resistant leukaemia model, a cell line taken over from BNML with the designation LT12 was selected. This BNML line has the advantage that it grows in vivo and in vitro.

Introduction (in vitro) of the human mdr1 gene into the genomic-DNA, by means of transfection, made the LT12 cells substance resistance. The transfection was effected using expression vector pFRCMV mdr1. 6, which contains an entire cDNA of the human mdr1 gene, controlled by an early accelerator for a CMV promoter followed by HBV polyadenylation signals. The transfected DNA segments were selected with mitoxantron and maintained under substance selection with 200 nM mitoxantron.

This procedure yielded a stable, substance-resistant LT12 cell line designated LT12/mdr.

End point flow cytometry

Cells can be identified on the basis of horizontal (size parameter) and vertical (structure parameter) light scatter using flowcytometry. The effects are measured on stimulation by 0.6 W of a 488 nm laser beam for each cell: horizontal light scatter, vertical light scatter (by a 488-nm band filter) and daunorubicin fluorescence (by a 550 nm long band filter). The daunorubicin content of the cell population can be investigated by combining the scatter values with the fluorescence values. At t=0 daunorubicin (final concentration 2 μM) and a experimental compound (final concentration 1.0 μM, 3.0 μM or 10 μM) are added to the cell suspension (2.10$^5$ cells/ml in RPMI-1640 medium without phenol red). The cells were incubated for 90 minutes at 37° C.

The intracellular daunorubicin concentration was determined using a flow cytometer by measuring their light fluorescence at stimulation with 488 nm laser radiation. RPMI-1640 medium without phenol red served as negative control. Each experiment used cyclosporin A (0.3, 1 and 3 μM) as effective substance.

Dead cells were identified by contrast staining with the non-vital dyes Hoechst 33258 (stimulation with 0.2 W of a UV laser beam by a 405 nm long passage filter). These dead cells and the detritus were always excluded from the analysis.

On-line flow cytometry

On-line flow cytometry is a modification of the normal flow cytometry method which permits the uninterrupted measurement of a sample over a period of several hours. At predetermined times the trial microcomputer stores the data from in each case 2000 cells in a so-called list mode file. Since all relevant parameters (e.g., size, structure, substance accumulation, etc.) of each cell are stored, it is possible to carry out comprehensive data analyses and renewed experiments.

The cell suspension was maintained at 37° C. in a reaction vessel with a thermostatic water jacket associated with the flow cell of the flow cytometer. The medium contained in the cells is pressed through the flow cell by means of air pressure. An additional inlet in the reaction vessel permits the addition of substances while the cells are observed. The method of on-line flow cytometry is therefore particularly suitable for the measurement of (fast) kinetic changes in intracellular substance concentrations.

In this type of experiment the measurement was commenced without daunorubicin in the cell suspension (2.10$^5$ cells/ml in RPMI-1640 medium without phenol red). At t=0 daunorubicin was added to the cells (final concentration 2 μM). The net uptake of daunorubicin by the cells was then measured for a period of 60 minutes until a steady state of substance accumulation was reached. At this moment the test compound was added to the cell suspension and the substance accumulation was again measured for 60 minutes. Cyclosporin A was added to the cell suspension as positive control substance.

The results confirm the suitability of the compound of the invention for this purpose. The untreated LT 12/mdr cells display a value of 23% daunorubicin fluorescence, non-resistant cells show 100% daunorubicin fluorescence. The comparative substance Cyclo-A shows 120% daunorubicin fluorescence at a concentration of 0.3 μMol, 110% at 1.0 μMol and 130% at 3 μMol.

Flezelastin yielded 60% daunorubicin fluorescence at 0.1 μMol, 110% at 0.3 μMol, 130% at 0.5 μMol, 130% at 1.0 μMol and 140% at 3.0 μMol.

Azelastin showed 50% daunorubicin fluorescence at 0.1 μMol, 70% at 0.3 μMol, 90% at 0.5 μMol, 110% at 1.0 μMol and 140% at 3.0 μMol.

What is claimed is:

1. A method of treating multi-drug resistance which comprises administering to a patient suffering therefrom an effective amount of a compound selected from the group consisting of compounds of the formula:

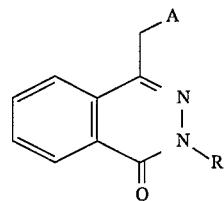

where A=phenyl (unsubstituted, mono- or multi-halogen substituted), H or $C_1$–$C_3$-alkyl, 2-furyl or 2-thienyl and R- is

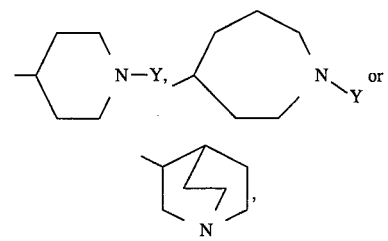

with Y=phenylalkyl or fluorphenyl alkyl as well as all physiological acceptable acid addition salts thereof, the compound of Formula II

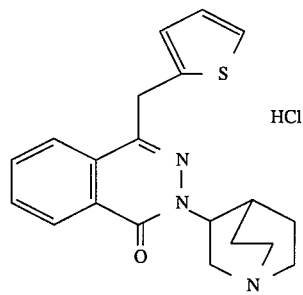

a compound of Formula III

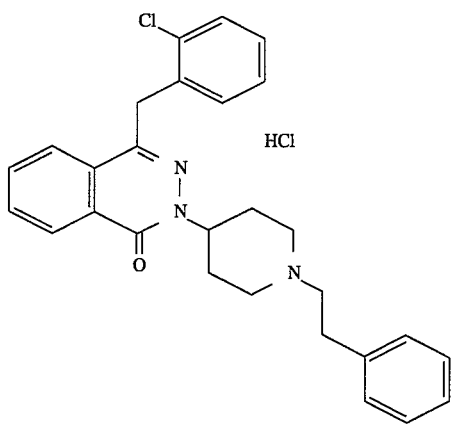

and flezelastine and its optical isomers.

2. A method of treating multi-drug resistance as set forth in claim 1 wherein the compound administered is the compound of Formula I.

3. A method of treating multi-drug resistance as set forth in claim 1 wherein the compound administered is the compound of Formula II.

4. A method of treating multi-drug resistance as set forth in claim 1 wherein the compound administered is the compound of Formula III.

5. A method of treating multi-drug resistance as set forth in claim 1 wherein the compound administered is selected from the group consisting of flezelastin and its optical isomers.

* * * * *